(12) United States Patent
Luo et al.

(10) Patent No.: US 12,130,226 B2
(45) Date of Patent: Oct. 29, 2024

(54) METHOD FOR EVALUATING INFLUENCE OF HUMIDITY ON ASPHALT-AGGREGATE ADHESION

(71) Applicant: WUHAN UNIVERSITY OF TECHNOLOGY, Wuhan (CN)

(72) Inventors: Rong Luo, Wuhan (CN); Wei Wang, Wuhan (CN); Chongzhi Tu, Wuhan (CN); Longchang Niu, Wuhan (CN); Xiang Wang, Wuhan (CN)

(73) Assignee: WUHAN UNIVERSITY OF TECHNOLOGY, Wuhan (CN)

( * ) Notice: Subject to any disclaimer, the term of this patent is extended or adjusted under 35 U.S.C. 154(b) by 281 days.

(21) Appl. No.: 17/721,340

(22) Filed: Apr. 14, 2022

(65) Prior Publication Data

US 2022/0326143 A1    Oct. 13, 2022

Related U.S. Application Data

(63) Continuation of application No. PCT/CN2021/120075, filed on Sep. 24, 2021.

(30) Foreign Application Priority Data

Apr. 9, 2021   (CN) .......................... 202110381579.0

(51) Int. Cl.
*G01N 19/04*      (2006.01)
*G01N 33/42*      (2006.01)
(Continued)

(52) U.S. Cl.
CPC ............. *G01N 19/04* (2013.01); *G06T 5/20* (2013.01); *G06T 5/70* (2024.01); *G06T 7/0002* (2013.01);
(Continued)

(58) Field of Classification Search
CPC .......... G01N 19/04; G01N 33/42; G06T 5/70; G06T 5/20; G06T 7/0002; G06T 2207/20032
(Continued)

(56) References Cited

FOREIGN PATENT DOCUMENTS

CN          105136603 A    *   12/2015
CN          105242030 A    *   1/2016
(Continued)

OTHER PUBLICATIONS

Translation CN_105806747_ (Year: 2016).*
(Continued)

*Primary Examiner* — Peter J Macchiarolo
*Assistant Examiner* — Monica S Young
(74) *Attorney, Agent, or Firm* — Jeenam Park

(57) ABSTRACT

Disclosed is method for evaluating influence of humidity on adhesion of asphalt-aggregate adhesion, the method includes the following steps: S1 putting multiple pull-out specimens into constant temperature and humidity phases with different relative humidity for curing, after the humidity reaches equilibrium, carrying out macroscopic mechanical pull-out test out and obtaining images of two aggregate surfaces of each broken pull-out specimen; S2 cropping the images, and then importing the cropped images into the Images Pro Plus software; S3 obtaining asphalt peeling rate according to the pixel value and calculation formula of asphalt peeling rate; S4 according to the asphalt peeling rate, asphalt cohesive energy and asphalt-aggregate binding energy, combined with calculation formula of asphalt-aggregate interface energy, obtaining asphalt-aggregate interface energy, and evaluating asphalt-aggregate adhesion according to the interface energy. This method realizes the quantitative evaluation of the adhesion of asphalt and aggregate under different humidity conditions.

8 Claims, 2 Drawing Sheets

(51) Int. Cl.
  *G06T 5/20*      (2006.01)
  *G06T 5/70*      (2024.01)
  *G06T 7/00*      (2017.01)
(52) U.S. Cl.
  CPC .... *G01N 33/42* (2013.01); *G06T 2207/20032* (2013.01)
(58) Field of Classification Search
  USPC .......................................................... 73/150
  See application file for complete search history.

(56) References Cited

FOREIGN PATENT DOCUMENTS

| | | | | |
|---|---|---|---|---|
| CN | 105806747 A | * | 7/2016 | |
| CN | 105891109 A | * | 8/2016 | |
| CN | 106290074 A | * | 1/2017 | ............. G01N 13/00 |
| CN | 109211904 A | * | 1/2019 | ............. G01N 21/84 |
| CN | 111855498 A | | 10/2020 | |
| CN | 111982806 A | * | 11/2020 | |
| CN | 113125340 A | | 7/2021 | |
| RO | 103413 B1 | | 12/1993 | |
| RU | 2686340 C1 | | 4/2019 | |
| WO | 2019223539 A1 | | 11/2019 | |

OTHER PUBLICATIONS

Translate CN105242030 (Year: 2016).*
Translate CN111982806 (Year: 2020).*
Translate CN105136603 (Year: 2016).*
Effect of relative humidity on the linear viscoelastic properties of asphalt mixtures Lei Xi a School of Transportation, Wuhan University of Technology, ScienceDirect Construction and Building Materials Construction and Building Materials vol. 271, Feb. 8, 2021 (Year: 2021).*
Translate CN-109211904 (Year: 2019).*
Wang Peng Asphalt and Aggregate Interface Adhesion Performance Research China Excellent Doctoral Master's Thesis Full-text Database (Master)Engineering Science and Technology II. Series 2411(Nov. 24, 2020) No. 2 Issue 7 pp. C034-C054.
Dong Wenjiao et al. studied the adhesion evaluation system of Shanxi architecture in Shanxi Apr. 11, 2016 (Apr. 11, 2016) Issue 11 vol. 42 pp. 122-123.
Study of cohesion and adhesion properties of asphalt concrete with computational materials science, Guangji Xu, Hao Wang.

* cited by examiner

METHOD FOR EVALUATING INFLUENCE OF HUMIDITY ON ASPHALT-AGGREGATE ADHESION

CROSS-REFERENCE TO RELATED APPLICATIONS

This application is a continuation of International Patent Application No. PCT/CN2021/120075, with an international filing date of Sep. 24, 2021, designating the United States, now pending, which is based on Chinese Patent Applications No. 2021103815790, filed on Apr. 9, 2021. The contents of these specifications are incorporated herein by reference.

FIELD OF THE DISCLOSURE

The disclosure relates to method for evaluating influence of humidity on asphalt-aggregate adhesion.

BACKGROUND

The existing theory believes that asphalt mixture is a three-phase composite system composed of asphalt, aggregates and air, in which the binding effect of asphalt and aggregate determines the overall performance of the asphalt mixture. Asphalt pavement has been under severe traffic load throughout its service life. It is exposed to harsh natural environments and has continuously developed various diseases, such as rutting, fatigue cracking, and water damage. Among them, water damage is closely related to the adhesion performance of asphalt and aggregate interface, and the main cause of the disease is that water invades the asphalt and aggregate interface. Under the action of external factors such as vehicle load and temperature stress, the asphalt and aggregate will peel off, which will reduce the performance of road surface.

The methods recommended in the current specification to evaluate the water stability of asphalt mixtures are water boiling method and water immersion method, but these methods are qualitative evaluation, which are greatly interfered by human factors, and it is impossible to evaluate the influence of gaseous water on the adhesion of the mixture. The traditional mechanical pull-out test is to adhere the pulling head filled with asphalt to the surface of stone, and evaluate the asphalt-aggregate adhesion through the maximum pulling force after tensile failure at the asphalt-aggregate interface and the peeling rate of the asphalt, but this method ignores that the asphalt oil film in the asphalt mixture is sandwiched between the two layers of aggregate, and the interface adhesion cracking may occur in any of the two layers. Therefore, from the perspective of material energy, the surface free energy theory quantitatively evaluates the adhesion between asphalt and aggregate through the adhesion work of asphalt and aggregate, the internal binding energy of asphalt and the stripping work of asphalt under the participation of water. However, the surface energy method only evaluates the adhesion of the material from the microscopic level, ignoring the macroscopic stress of the material, and there is little comparative analysis with other evaluation indexes, which fails to establish a good relationship. At the same time, the actual asphalt-aggregate failure is often mixed failure. It is difficult to obtain different failure ratios by surface energy method, which leads to the neglect of the actual failure situation when quantitatively characterizing the adhesion.

SUMMARY

Therefore, it is necessary to modify the calculation process of asphalt peeling rate by pull-out test, and a multi-scale evaluation method for the influence of humidity on the adhesion of asphalt and aggregate is proposed based on macroscopic pull-out test and microscopic surface energy test.

The purpose of this disclosure is to overcome the above technical deficiencies, provide a method to evaluate the impact of humidity on asphalt-aggregate adhesion, and solve the technical problems that the influence of humidity on the adhesion of asphalt-aggregate cannot be quantitatively evaluated in the prior art.

In order to achieve the above technical objectives, the technical solution of this disclosure provides a method for evaluating influence of humidity on the adhesion of asphalt-aggregate, which includes the following steps:

S1 putting multiple pull-out specimens into constant temperature and humidity phases with different relative humidity for curing, after the humidity reaches equilibrium, carrying out macroscopic mechanical pull-out test out and obtaining images of two aggregate surfaces of each broken pull-out specimen;

S2 cropping the images, and then importing the cropped images into the Images Pro Plus software to preprocess the images and obtaining pixel value of aggregate and asphalt;

S3 obtaining asphalt peeling rate according to the pixel value and calculation formula of asphalt peeling rate;

S4 according to the asphalt peeling rate, asphalt cohesive energy and asphalt-aggregate binding energy, combined with calculation formula of asphalt-aggregate interface energy, obtaining asphalt-aggregate interface energy, and evaluating asphalt-aggregate adhesion according to the interface energy.

The beneficial effects of this disclosure includes: putting multiple pull-out specimens into constant temperature and humidity phases with different relative humidity for curing, after the humidity reaches equilibrium, carrying out macroscopic mechanical pull-out test out and obtaining images of two aggregate surfaces of each broken pull-out specimen; cropping the images, and then importing the cropped images into the Images Pro Plus software to preprocess the images and obtaining pixel value of aggregate and asphalt; obtaining asphalt peeling rate according to the pixel value and calculation formula of asphalt peeling rate; according to the asphalt peeling rate, asphalt cohesive energy and asphalt-aggregate binding energy, combined with calculation formula of asphalt-aggregate interface energy, obtaining asphalt-aggregate interface energy, and evaluating asphalt-aggregate adhesion according to the interface energy. This method comprehensively considers multiple parameters to evaluate the influence of humidity on the adhesion of asphalt-aggregate through the interfacial energy of asphalt-aggregate, and realizes the quantitative evaluation of the adhesion of asphalt and aggregate under different humidity conditions. The larger the asphalt-aggregate interfacial energy is, the stronger the adhesion of asphalt and aggregate is.

BRIEF DESCRIPTION OF THE DRAWINGS

Accompanying drawings are for providing further understanding of embodiments of the disclosure. The drawings form a part of the disclosure and are for illustrating the principle of the embodiments of the disclosure along with the literal description. Apparently, the drawings in the description below are merely some embodiments of the disclosure, a person skilled in the art can obtain other drawings according to these drawings without creative efforts. In the figures.

DETAILED DESCRIPTION OF PREFERRED EMBODIMENTS

Figure 1:
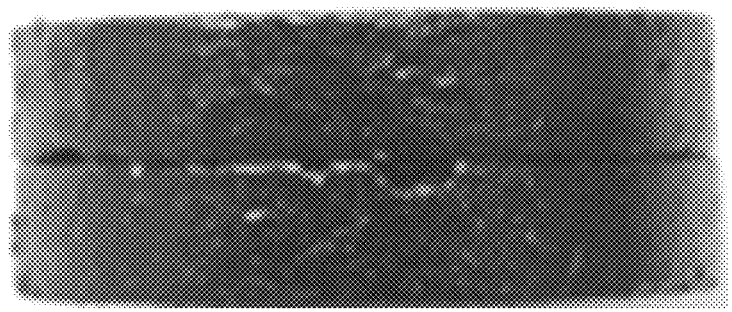
FIG. 1 is a schematic diagram of a pull-out specimen in Embodiment 1 of this disclosure.

This specific embodiment proposes a method for evaluating influence of humidity on asphalt-aggregate adhesion, including the following steps:

S0 Preparing the pull-out specimens, preheating two pieces of aggregate and asphalt, and then dripping the preheated asphalt on one surface of an aggregate, and covering another piece of aggregate on the asphalt and cooling to obtain the pull-out specimens; the aggregate is stone; thickness of the stone is 5-7 mm and diameter of the stone is 25-28 mm.

S1 Putting multiple pull-out specimens into constant temperature and humidity phases with relative humidity of 0-10%, 40-50%, 60-80%, and 90-100%, respectively for curing at 20-25° C. for 3-4 months, after the humidity reaches equilibrium, carrying out macroscopic mechanical pull-out test out and obtaining images of two aggregate surfaces of each broken pull-out specimen;

S2 Cropping the images, and then importing the cropped images into the Images Pro Plus software to preprocess the images and obtaining pixel value of aggregate and asphalt;

S3 Obtaining asphalt peeling rate according to the pixel value and calculation formula of asphalt peeling rate;

S4 Using plug-in method to obtain surface energy parameter of asphalt by measuring contact angle, using vapor adsorption method to obtain surface energy parameter of the aggregate, and calculating asphalt cohesive energy and asphalt-aggregate binding energy respectively according to surface energy parameters of the asphalt and the aggregate;

S5 According to the asphalt peeling rate, asphalt cohesive energy and asphalt-aggregate binding energy, combined with calculation formula of asphalt-aggregate interface energy, obtaining asphalt-aggregate interface energy, and evaluating asphalt-aggregate adhesion according to the interface energy.

Further, calculation formula of asphalt-aggregate interface energy is as follows:

$$W_E = \beta \times \Delta G^{aA} + (1-\beta) \times \Delta G^{cA}$$

where, $W_E$ represents interfacial energy, $\beta$ represents asphalt peeling rate, $\Delta G^{cA}$ represents asphalt cohesive energy, and $\Delta G^{aA}$ represents asphalt-aggregate binding energy.

Further, in step S2, the specific steps for obtaining the pixel value of aggregate and asphalt are as follows:

S21 Importing the cropped image into the Images Pro Plus software and displaying it in a drawing window;

S22 Converting the image to grayscale;

S23 Smoothing the image by a median filter of 3*3 window to further eliminate the noise formed in image shooting;

S24 Using Count and measure object and Histogram Based functions of the Images Pro Plus software to select the asphalt surface and the entire aggregate surface and calculating the pixel value.

In order to make the purpose, technical solutions, and advantages of this disclosure clearer, the following describes this disclosure in further detail with reference to the accompanying drawings and embodiments. It should be understood that the specific embodiments described here are only used to explain this disclosure, and are not used to limit this disclosure.

Embodiment 1

1. Using 70# matrix asphalt produced by a company in Hubei Province, China and limestone parent rock from a certain place to prepare pull-out specimens and conduct pull-out test tests:

Using a core drilling machine with a hole diameter of 25 mm to drill the limestone mother rock to core samples, and then use a cutter to cut the stone into thin slices with a thickness of 5 mm (in other embodiments, the thickness of the stone can also be 6 mm or 7 mm, and the diameter can be 26 mm or 27 mm). Using the same number of sandpapers to polish the thin slices for the same time. Using a spiral micrometer with an accuracy of 0.001 mm to measure the thickness of the two stones stacked together. Putting the stone and 70# matrix asphalt in an oven at the temperature required by the asphalt mixture design specification. Then dropping a little bit of hot asphalt on the surface of one stone, and quickly cover the other stone. Using a screw micrometer to measure the thickness of the stone-asphalt-stone. When the thickness is too large, squeezing the upper and lower surfaces of the test piece until the thickness is appropriate. At this time, the thickness difference between the two measurements is 20 microns. After cleaning the spilled asphalt with clean cloth, the asphalt is placed on a flat operating table and cooled for 30 min. The obtained specimens are shown in FIG. 1. After the specimens are formed, putting the specimens into constant temperature and humidity box with relative humidity of 0-10%, 40-50%, 60-80%, and 90-100%, respectively for curing for 3 months, different relative humidity gradients can also be set in other embodiments, such as 5%, 40%, 70%, 90% relative humidity, the temperature is kept at 20° C., At the same time, as a comparison, a control group of one-day liquid water curing is set, and the temperature is 20° C. In other embodiments, it can also be other temperatures between 20 and 25° C. The corresponding gaseous water molecule concentrations under different relative humidity are shown in Table 1.

TABLE 1

| Relative humidity corresponding to gaseous water molecular concentration (20° C.) | | | | |
|---|---|---|---|---|
| Relative humidity | 0% | 50% | 80% | 100% |
| Gaseous water molecular concentration in air/g · m⁻³ | 0 | 8.64 | 13.82 | 17.27 |

Using 406 quick-drying glue to glue one side of the "sandwich" specimen to a lower fixture. After standing at room temperature for 10 minutes, transferring the lower fixture and the specimen to an MTS environment box, fixing the lower fixture, and then dropping a little glue on the surface of the top stone. At the same time, installing the upper clamp on the guide rod above the instrument. Turning on the MTS instrument, setting the control mode to "force mode", and setting the pressure to 12 N. At this time, the upper fixture will gradually drop with the upper guide rod and contact and squeeze with the upper surface of the specimen dripped with glue. After maintaining the squeezed state for 10 minutes, changing the pressure to ON, and switching the control mode to "displacement mode".

Figure 2:
FIG. 2 is the asphalt surface of the damaged stone in Embodiment 1 of this disclosure.

The test adopts uniaxial direct tensile test, setting the tensile rate to 0.5 mm/min, and recording the data of tensile force change with the increase of tensile length. When the tensile force is close to 0, the specimen has been completely destroyed at this time. Taking pictures of the surface of two stones with asphalt in each group. The asphalt surface of one of the damaged specimens is shown in FIG. 2.

2. Cropping the image, using Images Pro Plus software to obtain the pixel value of the stone and asphalt, and calculating the modified asphalt peeling rate:

The two images of the obtained specimens were uniformly cut according to the standard that only exposed the circular stone interface. Importing an image into the Images ProPlus software, calling a program to convert the color droplet image into a grayscale image, and using a 3*3 window to perform median filtering on the image, Then continuing to call the Count and measure object function of the software, by adjusting the gray value range under the Histogram Based window, the whole circular aggregate section is completely selected to calculate the entire pixel value of circular stone. Then continuing to adjust the gray value range, so that all the asphalt surface is fully selected to calculate the entire pixel value of the peeling asphalt. There are two failure sections after each group of pull-out tests, and the pixel value of these two failure sections need to be calculated.

Calculating the modified asphalt peeling rate $\beta$ according to formula (1):

$$\text{Peeling rate } \beta = \sum \frac{\text{Pixel value of circular stone} - \text{Pixel value of asphalt surface}}{\text{Pixel value of circular stone}} \quad (1)$$

where $\Sigma$ means the sum of the two stones of the specimens.

Through software calculation, the pixel value of circular section of each specimen is 58544, and then obtaining the pixel value of the asphalt surface in turn and putting it into the formula to obtain the peeling rate of the asphalt with different relative humidity. The results are shown in Table 2.

TABLE 2

Peeling rate of specimens under different humidity

| Relative humidity | 0% | 50% | 80% | 100% | 1 d liquid water |
|---|---|---|---|---|---|
| Peeling rate (%) | 0.4 | 10.3 | 22.6 | 52.2 | 88.3 |

3. Using plug-in method and vapor adsorption method to obtain surface energy parameter of asphalt.

Using plug-in method to obtain surface energy parameter of asphalt by measuring contact angle, using vapor adsorption method to obtain surface energy parameter of the stone, and calculating asphalt cohesive energy and asphalt-aggregate binding energy respectively according to surface energy parameters of the asphalt and the stone, as shown in Table 3.

TABLE 3

Surface energy parameters of asphalt and aggregates under different conditions

| Surface energy (ergs · cm$^{-2}$) | 0 | 50 | 80 | 100 | liquid water |
|---|---|---|---|---|---|
| Asphalt cohesive energy $\Delta G^{cA}$ | 43.10 | 43.10 | 43.10 | 43.10 | 43.10 |
| Asphalt-aggregate binding energy $\Delta G^{aA}$ | 94.50 | 38.22 | 11.90 | 0.68 | 41.53 |

Calculation formula of asphalt-aggregate interface energy is as follows:

$$W_E = \beta \times \Delta G^{aA} + (1-\beta) \times \Delta G^{cA} \quad (2)$$

where $W_E$ represents interfacial energy, $\beta$ represents asphalt peeling rate, $\Delta G^{cA}$ represents asphalt cohesive energy, and $\Delta G^{aA}$ represents asphalt-aggregate binding energy.

Calculating the joint macro and micro interface energy indicators:

Substituting the asphalt peeling rate, asphalt cohesive energy and asphalt-aggregate binding energy into formula (2) to calculate the asphalt-aggregate interface energy.

Figure 3:
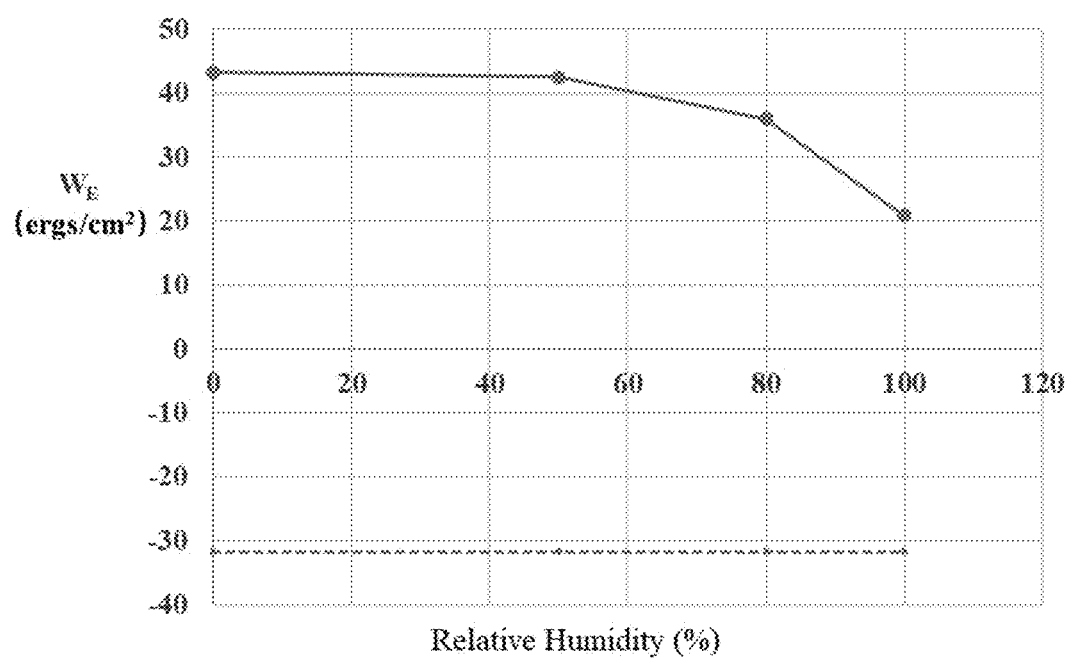
FIG. 3 is the asphalt-aggregate interface energy under different relative humidity in Embodiment 1 of this disclosure.

It can be seen from FIG. 3 that as humidity (relative humidity) increases, asphalt-aggregate interface energy gradually decreases, and the adhesion between asphalt and aggregate is getting worse and worse, especially under high humidity conditions, the adhesion is significant decline. And this index is consistent with the traditional asphalt-aggregate binding energy evaluation index based on the surface energy method, and the change of cohesive cracking is considered, combined with the surface energy method to evaluate the adhesion.

It can be seen that the method proposed by this disclosure combines the macro and microscopic evaluation of asphalt-aggregate adhesion parameters, which can quantitatively evaluate the adhesion of asphalt and aggregate under different humidity conditions on multi-scales. Furthermore, the degree of influence on the adhesion of asphalt and aggregate under different humidity can be judged according to the magnitude of the asphalt-aggregate interface energy. The larger the asphalt-aggregate interfacial energy is, the stronger the adhesion of asphalt and aggregate is.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A method for evaluating influence of humidity on adhesion of asphalt-aggregate, including the following steps:
    S1 putting multiple pull-out specimens into constant temperature and humidity phases with different relative humidity for curing, after the humidity reaches equilibrium, carrying out macroscopic mechanical pull-out test on the pull-out specimen until the specimen is broken off the aggregate and obtaining images of two aggregate surfaces of each broken pull-out specimen, wherein the aggregate is stone;
    S2 cropping the images, and then preprocessing the images and obtaining pixel value of aggregate and asphalt;

S3 obtaining asphalt peeling rate according to the pixel value and calculation formula of asphalt peeling rate, wherein the calculation formula of asphalt peeling rate is as follows:

Peeling rate β=ΣPixel value of stone−Pixel value of asphalt surface/Pixel value of stone, wherein Σ represents a sum of the two stones of the specimens;

S4 according to the asphalt peeling rate, asphalt cohesive energy and asphalt-aggregate binding energy, combined with calculation formula of asphalt-aggregate interface energy, obtaining asphalt-aggregate interface energy, and evaluating asphalt-aggregate adhesion according to the interface energy, wherein calculation formula of asphalt-aggregate interface energy is as follows:

$$W_E = \beta \times \Delta G^{aA} + (1-\beta) \times \Delta G^{cA},$$

wherein $W_E$ represents interfacial energy, β represents asphalt peeling rate, $\Delta G^{cA}$ represents asphalt cohesive energy, and $\Delta G^{aA}$ represents asphalt-aggregate binding energy.

2. The method for evaluating influence of humidity on adhesion of asphalt-aggregate according to claim 1, in step S2, the specific steps for obtaining the pixel value of aggregate and asphalt are as follows:
S21 displaying the cropped image in a drawing window;
S22 converting the image to grayscale;
S23 filtering the image using a median filter with a 3×3 sampling window;
S24 selecting the asphalt surface and the entire aggregate surface of the image and calculating the pixel value.

3. The method for evaluating influence of humidity on adhesion of asphalt-aggregate according to claim 1, wherein:
before step S4, the method further includes obtaining surface energy parameter of asphalt by measuring contact angle, using vapor adsorption method to obtain surface energy parameter of the aggregate, and calculating asphalt cohesive energy and asphalt-aggregate binding energy respectively according to surface energy parameters of the asphalt and the aggregate.

4. The method for evaluating influence of humidity on adhesion of asphalt-aggregate according to claim 1, in step S1, putting multiple pull-out specimens into constant temperature and humidity phases with relative humidity of 0-10%, 40-50%, 60-80%, and 90-100%, respectively for curing.

5. The method for evaluating influence of humidity on adhesion of asphalt-aggregate according to claim 4, in step S1, duration of the curing is 3-4 months.

6. The method for evaluating influence of humidity on adhesion of asphalt-aggregate according to claim 4, in step S1, temperature of the curing is 20-25° C.

7. The method for evaluating influence of humidity on adhesion of asphalt-aggregate according to claim 1, before step S1, the method further includes: preparing the pull-out specimens, preheating two pieces of aggregate and asphalt, and then dripping the preheated asphalt on one surface of an aggregate, and covering another piece of aggregate on the asphalt and cooling to obtain the pull-out specimens.

8. The method for evaluating influence of humidity on adhesion of asphalt-aggregate according to claim 1, thickness of the stone is 5-7 mm and diameter of the stone is 25-28 mm.

* * * * *